United States Patent [19]

Odencrantz et al.

[11] Patent Number: 5,043,928

[45] Date of Patent: Aug. 27, 1991

[54] RESAMPLING SYSTEM USING DATA INTERPOLATION TO ELIMINATE TIME EFFECTS

[75] Inventors: Kirk C. Odencrantz; Louis Hlousek, both of Reno; Scot R. Weinberger, Sparks, all of Nev.

[73] Assignee: Linear Instruments, Reno, Nev.

[21] Appl. No.: 367,818

[22] Filed: Jun. 19, 1989

[51] Int. Cl.⁵ .............................................. G06G 7/30
[52] U.S. Cl. .................................. 364/577; 364/498; 436/43
[58] Field of Search ............... 364/577, 723, 581, 582, 364/571.02, 573, 497–499, 550, 551.01, 553; 73/863, 864; 436/8, 34, 43, 164; 250/564, 565

[56] References Cited

U.S. PATENT DOCUMENTS

| | | | |
|---|---|---|---|
| 4,169,125 | 9/1979 | Rodriguez et al. | 364/497 X |
| 4,244,803 | 1/1981 | Aladjem et al. | 436/516 |
| 4,627,008 | 12/1986 | Rosenthal | 364/550 |
| 4,636,360 | 1/1987 | Sakurada et al. | 364/499 X |
| 4,642,778 | 2/1987 | Hieftje et al. | 364/498 |
| 4,658,367 | 4/1987 | Potter | 364/553 |
| 4,794,540 | 12/1988 | Gutman et al. | 364/577 X |
| 4,802,102 | 1/1989 | Lacey | 364/572 |
| 4,807,148 | 2/1989 | Lacey | 364/577 X |
| 4,817,024 | 3/1989 | Saigoh | 364/577 |
| 4,912,661 | 3/1990 | Potter | 364/550 |

OTHER PUBLICATIONS

*Mathematical Elements for Computer Graphics*, Rogers et al.; McGraw-Hill, pp. 116–121.
*Numerical Recipes in C*, Press et al., Cambridge University Press; pp. 85–98.

*Primary Examiner*—Joseph L. Dixon
*Attorney, Agent, or Firm*—Skjerven, Morrill, MacPherson, Franklin & Friel

[57] ABSTRACT

Absorbance and wavelength data which is generated by a liquid chromatography apparatus is orthogonalized and resampled by a cubic splining technique in order to provide a smooth spectra curve showing absorbance versus wavelength, with the time factor eliminated. This has the advantage of eliminating from the data any changes in the sample over time. The method results in the orthogonalization with respect to time of the data. The invention is applicable to analysis of data other than liquid chromatography data. Higher or lower order curve fitting techniques may be used instead of the cubic splining analysis method.

8 Claims, 4 Drawing Sheets

O MEASURED
+ ORTHOGANALIZED
  OR SAMPLED

RESAMPLING SYSTEM USING DATA INTERPOLATION TO ELIMINATE TIME EFFECTS

MICROFICHE APPENDIX

A Microfiche Appendix is attached including 1 fiche and 34 frames total, showing a computer program in accordance with the invention.

BACKGROUND OF THE INVENTION

1. Field of the Invention

This invention relates to interpolation of data as derived from scientific instruments or similar sources. More specifically, the invention relates to time dependent spectroscopy and to spectrophotometry of chemical samples, and to interpolation of chromatographic absorbances in both the time-absorbance plane, and the wavelengthabsorbance plane.

2. Description of the Prior Art

Liquid chromatography is a well known technique for analyzing fluids. As is well known in liquid chromatography, light of varying wavelengths is passed through a sample cell containing the fluid to be analyzed. A detection and measuring device then measures the amount of light that passes through the sample at a variety of different wavelengths. The resulting data is referred to as chromatographic data. The data is typically represented as a chromatogram. The absorbance data of a chromatogram may be written as a function AU (absorbance units)=f (wavelength, time). Thus, the absorbance is a single valued function in the so-called absorbance-wavelength-time space. That is to say the absorbance, wavelength, and time may be plotted as three dimensions in a three dimensional graph.

Polychromatic data, i.e. data taken at various wavelengths, from a liquid chromatography apparatus, is therefore represented as discrete points on the surface of the wavelength, time, absorbance function. Each measured absorbance is determined by a wavelength and a time, that is, $AU = f(\omega, t)$. A high speed scanning absorbance monitor in the liquid chromatographic apparatus typically measures each absorbance point for each wavelength sequentially with an inherent time delay between each point. Thus the absorbance may be mathematically represented as follows:

$$AU = f(\omega_1, t_1)$$
$$AU = f(\omega_2, t_2)$$
$$AU = f(\omega_3, t_3)$$
.
.
.
$$AU = f(\omega_n, t_n)$$
$$AU = f(\omega_1, t_{n+1})$$
$$AU = f(\omega_2, t_{n+2})$$
.
.
.
$$AU = f(\omega_n, t_{2n})$$
$$AU = f(\omega_1, t_{2n+1})$$
.
.
.

The nature of a liquid chromatographic apparatus or any other scientific instrument is that data must be taken over time The result of the time delay between taking of the various data points is that the absorbances at each of the wavelengths are not measured simultaneously. This situation is shown in FIG. 1. For instance, as the concentrations of the chemical compounds in the fluid in the sample change over time, the measured absorbances change. However, there is a problem in that an accurate comparison to produce meaningful results of the absorbances from several wavelengths requires that ideally all of the absorbances be taken at the same time. This ideal situation is shown in FIG. 4. Thus the data in FIG. 4 is shown as being orthogonal to the time axis. The ideal situation is not obtainable in reality in terms of taking actual measurements.

It is therefore desirable to have a method for achieving the elimination of the effect of time delay from the data, so as to provide an accurate representation of the absorbance as a function of wavelength. Only by providing such a representation is it possible to accurately characterize the constituents of the sample which is being tested. The prior art does not permit such an accurate characterization

SUMMARY OF THE INVENTION

In accordance with the invention, the effect of the time factor is eliminated from measured data pertaining to physical events. The method of the invention in the preferred embodiment eliminates the time delay factor from measured data. and provides an accurate depiction of the relationship between the remaining measured data. In accordance with the invention, since the instrument which takes the data is not capable of measuring the absorbances of multiple wavelengths at the same time, the measured data is orthogonalized with respect to time. In the preferred embodiment of the invention cubic splines, i.e. third order equations which represent a surface geometrically, are used to construct smooth curves (i.e., interpolate) between all measured points in the two-dimensional time-absorbance plane for each wavelength. The smooth curve so constructed defines the absorbance at any time for each wavelength. With the set of curves thus defined for several wavelengths, the absorbance at any time for each wavelength may be determined. Thus, absorbance values for each wavelength may be plotted geometrically or displayed numerically.

The sampling technique in accordance with the invention is performed for the curve of each wavelength at which data has been taken. Therefore a complete spectra is created using the orthogonalized data and using the absorbance-wavelength plane at the time of the desired spectra. The absorbances of each measured wavelength in the plane are splined by using the cubic splining technique to construct a smooth spectra curve. All the points of the spectra are for the same instant in time, thereby eliminating any errors caused by changes in concentration of the sample fluid over time In accordance with the invention an orthogonalization and resampling of data as described above may be performed for data other than that produced by a liquid chromatographic apparatus. The invention is applicable generally to data having two or more dimensions relative to time, where it is desired to remove the effect of time delay and show the remaining dimensions of data in terms of their relationship to each other. The invention provides for, in one embodiment, sampling a single valued function of two or more variables where instrumental or other limitations give a sampling interval that is not orthogonal in two of the dimensions. and it is desired that they be orthogonal.

In other embodiments of the invention, well-known curve fitting methods other than cubic splines (i.e., third order equations), such as linear equations, quadratic equations, or polynomials of the fourth or higher order are used as an alternative to cubic splines to perform the interpolation in two dimensions.

The Microfiche Appendix shows a computer program in accordance with the invention.

DETAILED DESCRIPTION OF THE INVENTION

Figure 2:
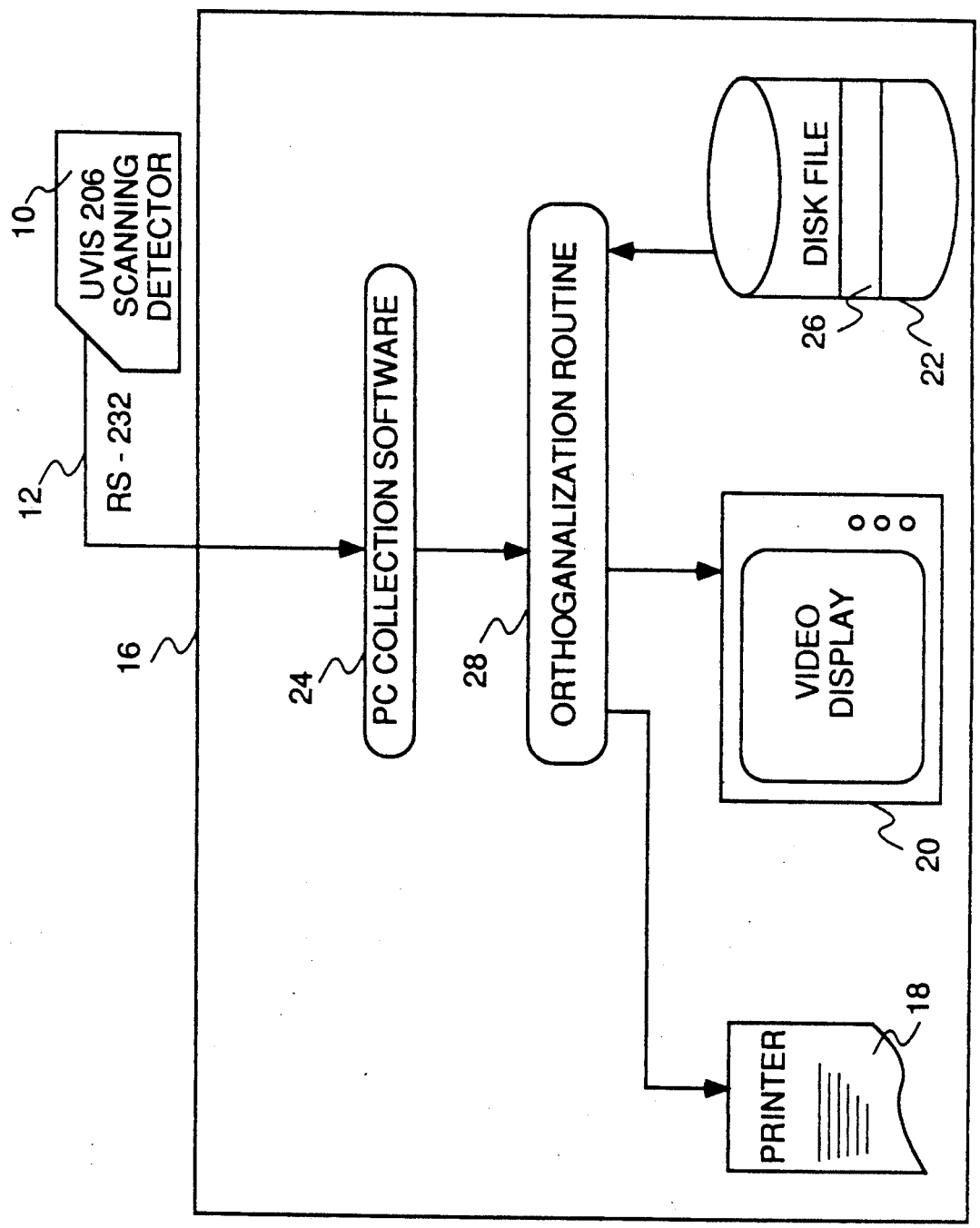
FIG. 2 shows an apparatus in accordance with the invention

In accordance with the invention, an apparatus as shown in FIG. 2 is used conventionally to acquire chromatographic data from a scanning detector 10 such as the UVIS 206 commercially available from Linear Instruments, Reno, Nev. The scanning detector 10 conventionally provides data as a "scan," i.e., a set of sequentially measured absorbance values from a single pass through all the desired wavelengths. The data so acquired (one or more scans) is conventionally provided via an RS-232 interface 12 to a computer 16, such as an IBM PC (personal computer) compatible computer. The computer 16 conventionally includes a printer 18, video display 20, and disk drive (i.e., disk file) 22. Installed on the computer 16 are computer programs 24, 28 which collect the data and save the data to chromatogram disk files 26 on the disk drive 22 and orthogonalize the data by an orthogonalization routine 28. A computer program 28 as used in the preferred embodiment of the invention is shown in the Microfiche Appendix of this patent disclosure. The PC collection software program 24 is conventional.

The Microfiche Appendix shows a computer program 28 source code listing in the well known C language in accordance with the invention. This computer program 28 reads data from a file 26 containing the data collected by the collection program 24. Program 28 orthogonalizes and then returns the resulting spectra values as a tabular result. Other portions of the computer program (not shown) conventionally provide plot, print, and saving data to disk features The mathematical concept of a spline is well known, and is derived from its physical counterpart, the loftsman's spline. A physical spline is a long narrow flexible strip used to provide smooth curves between fixed points.

A mathematical spline is a method of mathematically fitting a curve through a series of data points. Splines may be of an desired degree—first, second, third, etc. A first order spline is thus a linear equation (i.e., a first order polynomial); a second order spline is a quadratic equation; a third order spline is a cubic spline. Cubic splines are favored in the art, using a series of cubic splines with each segment spanning only two data points. (See *Mathematical Elements for Computer Graphics*, David F. Rogers and J. Alan Adams, McGraw-Hill, pp. 116-121)

Figure 3:
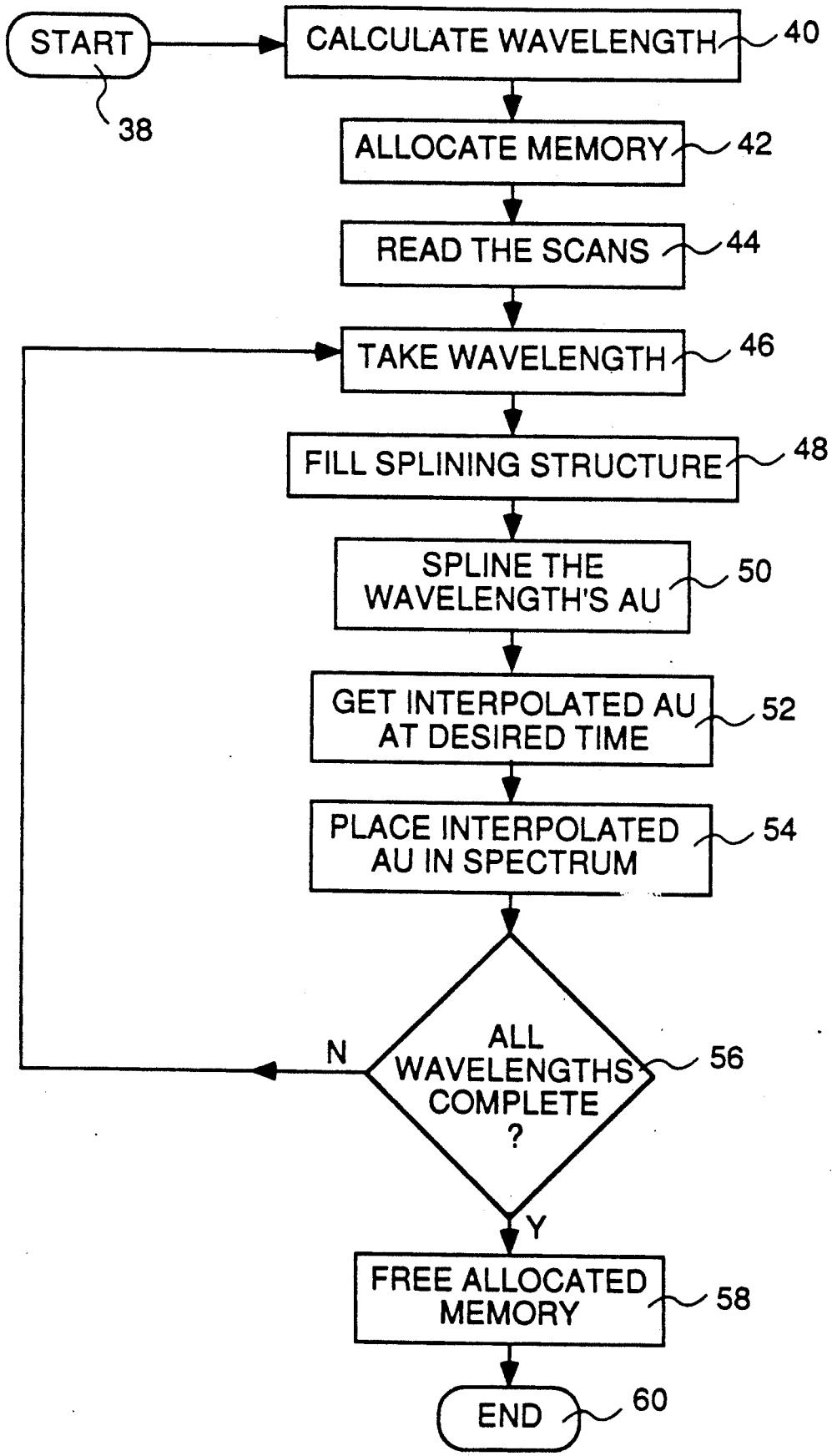
FIG. 3 shows a block diagram of software of one embodiment of the invention.

FIG. 3 shows in a flow chart the computer program described above in accordance with the invention.

Figure 1:
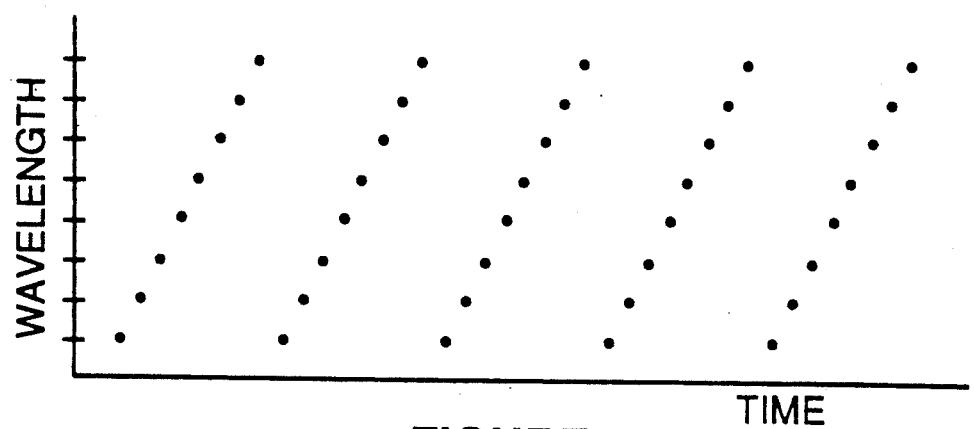
FIG. 1 shows a prior art plot of wavelength versus time.

After starting at start step 38, at the calculate wavelength step 40, the scans and their positions within the chromatogram file 26 (see FIG. 2) that are to be used for the interpolation are determined. Using the positions within the chromatogram file 26, these scans are read from the file 26 in a subsequent step as described below. The scans are the raw data as shown in FIG. 1, including the absorbance data.

At the allocate memory step 42, (see FIG. 3) the program assigns sufficient computer main memory to accept all the scan data from the chromatogram data file 26 (see FIG. 2). Then in read the scans step 44, the chromatogram data is read from the chromatogram disk files 26 to the computer main memory.

Then at take wavelength step 46, the program repetitively performs steps 46 to 54 for each wavelength at which data was taken. At fill the splining structure step 48, an array of absorbances is filled with the AU (absorbance units) values of the current wavelength from each of the scans. This array is combined with other fields that the splining algorithm will use to store the results of the spline to form the splining structure. A "structure" conventionally is used in the C programming language to mean a method of organizing data. Thus, referring to FIG. 1, for one wavelength (i.e., a horizontal line), the absorbance value for each scan (i.e., the slanted line defined by one of the series of data points) is provided to the splining structure Then in spline the wavelength's AU step 50, for the one wavelength, cubic splines are used to form a smooth curve between all measured points in the time-absorbance plane (see FIG. 5). The smooth curve thus defines the absorbance at any time for the current wavelength. The curve is drawn so as to connect the measured data points (denoted by dots).

At spline the wavelength's AU step 50, if not enough scans are available to accurately spline the absorbance values, then a linear interpolation is made in place of a cubic spline to form a curve. Preferably four scans are required on each side of the desired time for the orthogonalized spectrum, for cubic splining.

Figure 5:
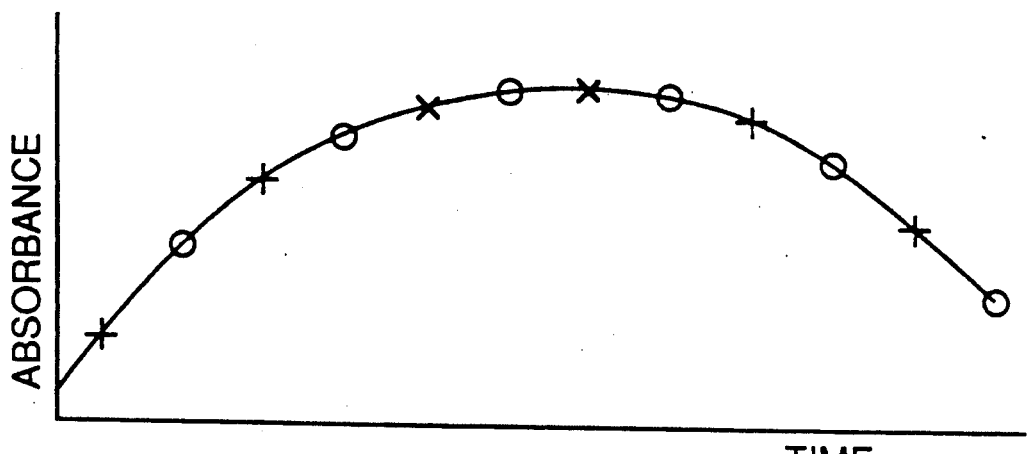
FIG. 5 shows a plot of absorbance versus time in accordance with the invention.

With the absorbance curve so drawn, in get interpolated AU at desired time step 52, the points on the curve of FIG. 5 between the data points are the orthogonalized data points (denoted by x's), giving the absorbance at any time for the current wavelength.

Figure 4:
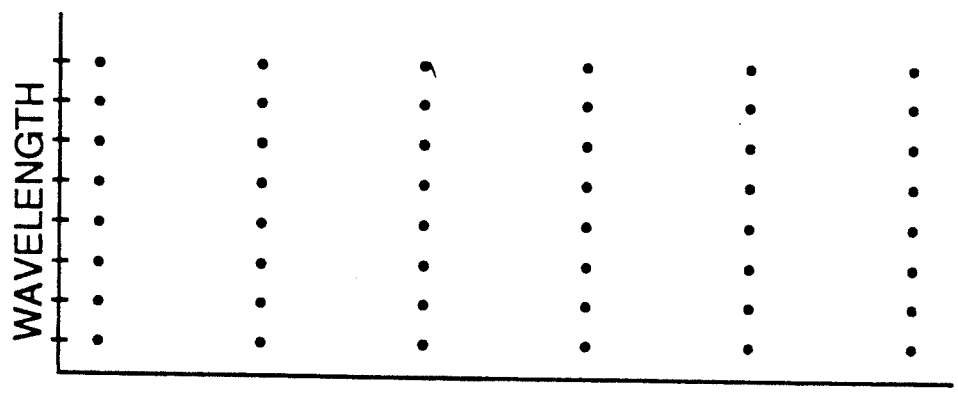
FIG. 4 shows a plot of wavelength versus time orthogonalized in accordance with the invention.
Figure 6:
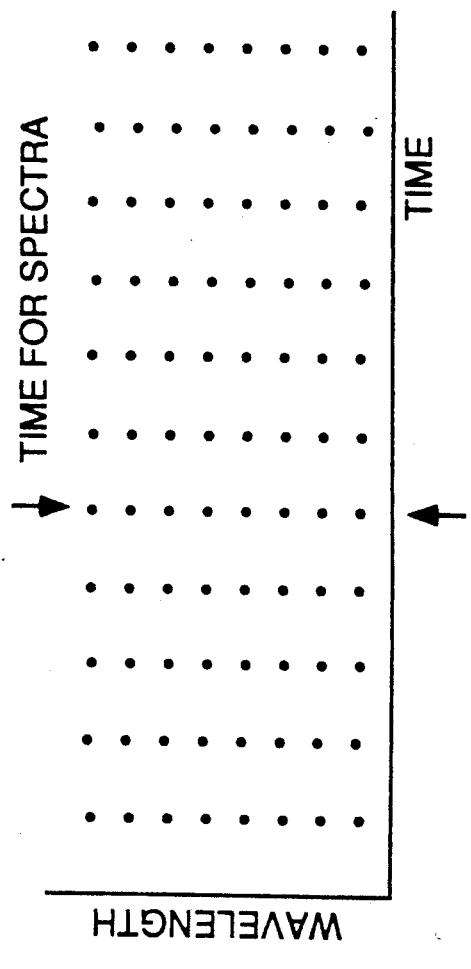
FIG. 6 shows a plot of wavelength versus time in accordance with the invention.

Then at place interpolated AU in spectrum step 54, the orthogonalized AU values from the curve in FIG. 5 are resampled (i.e., the one at the desired time is selected) and placed in the orthogonalized spectrum as shown in FIG. 6. The computer program in the preferred embodiment returns only a single orthogonalized spectrum; in other embodiments, multiple orthogonalized spectra are returned. FIG. 6 (showing an orthogonalized wavelength/time plot similar to that of FIG. 4) indicates an orthogonalized set of AU values for discrete points in time (i.e., the vertical line indicated by the arrows), over a range of wavelengths.

The above steps 46 to 54 are repeated for each wavelength as determined by all wavelengths complete step 56 When all the wavelengths are complete, then in free allocated memory step 58 the memory allocated in step 42 is freed, and the program ends at end step 60.

Figure 7:
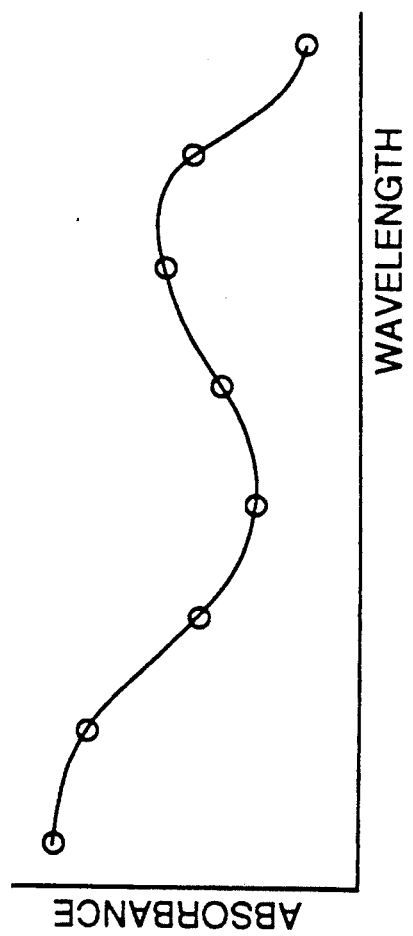
FIG. 7 shows a spectrum of absorbance versus wavelength in accordance with the invention.

Then the absorbances of each measured wavelength are conventionally splined in a second splining operation (not shown) to construct a smooth spectral curve for graphical display as shown in FIG. 7. All the points in the spectrum in FIG. 7 represent the same instant in time, thus eliminating measurement errors caused by changes in concentration, temperature, etc. of the sample over time.

The computer program as depicted in FIG. 3 is shown in detail in the Microfiche Appendix. The computer program of the Microfiche Appendix includes comments describing its operation.

This patent disclosure includes copyrightable material The copyright owner gives permission for the facsimile reproduction of material in Patent Office files, but reserves all other copyright rights.

The above description of the invention is illustrative and not limiting. Further embodiments to the invention will be apparent to one of ordinary skill in the art in light of the invention.

We claim:

1. A method for collecting and analyzing data comprising the steps of:
   collecting data having at least two variables taken over a discrete time period;
   orthognoalizing a function of a first variable with respect to time for a plurality of values of a second variable wherein the function of the first variable is at a plurality of values of the second variable and the first and second variables are independent to one another;
   interpolating data points of the function of the first variable with respect to time; and
   determining a relationship between the first variable and the second variable with respect to time.

2. The method of claim 1 wherein the first and second variables comprise variables relating respectively to the absorbance of light from a chromatographic sample and to the wavelength of the light.

3. The method of claim 1 wherein the step of interpolating comprises the step of determining a set of linear functions in two dimensions.

4. The method of claim 1 wherein the step of interpolating comprises the step of determining a set of quadratic functions in two dimensions.

5. The method of claim 1 wherein the step of interpolating comprises the step of determining a set of cubic functions in two dimensions.

6. The method of claim 1 wherein the step of interpolating comprises the step of determining a set of nth order functions in two dimensions, where n exceeds three.

7. The method of claim 5 wherein the step of determining comprises the step of fitting curves by use of cubic splines.

8. An instrument comprising:
   means for collecting data over a period of time having at least two variables;
   means for orthogonalizing a first variable with respect to time for a plurality of values of a second variable wherein the function of the first variable is at a plurality of values of the second variable and the first and second variables are independent to one another;
   means for interpolating data points of the function of the first variable with respect to time; and
   means for determining a relationship between the first variable and the second variable with respect to time.

* * * * *